United States Patent [19]
Ashmead et al.

[11] Patent Number: 6,166,071
[45] Date of Patent: Dec. 26, 2000

[54] ZINC AMINO ACID CHELATES HAVING LIGANDS COMPRISED OF GLYCINE AND A SULFUR-CONTAINING AMINO ACIDS

[75] Inventors: Stephen D. Ashmead; David C. Wheelwright, both of Clearfield, Utah

[73] Assignee: Albion International, Inc., Clearfield, Utah

[21] Appl. No.: 09/524,399

[22] Filed: Mar. 13, 2000

[51] Int. Cl.[7] .......................... A61K 31/315; C07F 3/06; A23K 1/175
[52] U.S. Cl. ..................... 514/494; 556/134; 426/74
[58] Field of Search .................. 556/134; 426/74; 514/494

[56] References Cited

U.S. PATENT DOCUMENTS

| | | | |
|---|---|---|---|
| 3,925,433 | 12/1975 | Abdel-Monem | 260/438.5 R |
| 4,020,158 | 4/1977 | Ashmead | 424/177 |
| 4,021,569 | 5/1977 | Abdel-Monem | 424/289 |
| 4,039,681 | 8/1977 | Abdel-Monem | 424/289 |
| 4,167,564 | 9/1979 | Jensen | 424/177 |
| 4,216,143 | 8/1980 | Ashmead | 260/113 |
| 4,216,144 | 8/1980 | Ashmend | 260/115 |
| 4,425,280 | 1/1984 | Ho | 260/429.9 |
| 4,559,152 | 12/1985 | Ashmead | 204/72 |
| 4,678,854 | 7/1987 | Abdel-Monem | 556/149 |
| 4,725,427 | 2/1988 | Ashmead | 424/44 |
| 4,764,633 | 8/1988 | Anderson | 556/50 |
| 4,774,089 | 9/1988 | Ashmead | 424/157 |
| 4,830,716 | 5/1989 | Ashmead | 204/72 |
| 4,863,898 | 9/1989 | Ashmead | 514/6 |
| 4,956,188 | 9/1990 | Anderson | 426/74 |
| 5,061,815 | 10/1991 | Leu | 556/118 |
| 5,278,329 | 1/1994 | Anderson | 556/50 |
| 5,332,579 | 7/1994 | Umbdenstock | 424/639 |
| 5,430,164 | 7/1995 | Abdel-Monem | 556/2 |
| 5,504,055 | 4/1996 | Hsu | 504/121 |
| 5,583,243 | 12/1996 | Abdel-Monem | 556/49 |
| 5,885,610 | 3/1999 | Anderson | 424/438 |

FOREIGN PATENT DOCUMENTS

0377526B1  12/1995  European Pat. Off. .

*Primary Examiner*—Porfirio Nazario-Gonzalez
*Attorney, Agent, or Firm*—Thorpe, North & Western, LLP

[57] ABSTRACT

A zinc amino acid chelate formulation is disclosed comprising zinc ions being chelated by an amino acid ligand mixture comprising glycine and a sulfur-containing amino acid wherein the ligand to zinc molar ratio is from about 1:1 to 2:1 and wherein the glycine to sulfur-containing amino acid molar ratio is between about 1:6 to 6:1.

37 Claims, No Drawings

ZINC AMINO ACID CHELATES HAVING LIGANDS COMPRISED OF GLYCINE AND A SULFUR-CONTAINING AMINO ACIDS

FIELD OF THE INVENTION

The present invention relates to amino acid chelates comprised of zinc, a sulfur-containing amino acid, and glycine having a ligand to metal molar ratio from about 1:1 to 2:1. By adding glycine and a sulfur-containing amino acid as a ligand mixture, a desired zinc weight percentage may be more easily achieved and the zinc becomes more bioavailable than traditional zinc sources.

BACKGROUND OF THE INVENTION

Amino acid chelates are generally produced by the reaction between $\alpha$-amino acids and metal ions having a valence of two or more to form a heterocyclic ring structure. In such a reaction, the positive electrical charge of the metal ion is neutralized by the electrons available through the carboxylate or free amino groups of the $\alpha$-amino acid.

Traditionally, the term "chelate" has been loosely defined as a combination of a metallic ion bonded to one or more ligands forming heterocyclic ring structures. Under this definition, chelate formation through neutralization of the positive charges of the divalent metal ions may be through the formation of ionic, covalent or coordinate covalent bonding. An alternative and more contemporary definition of the term "chelate" requires that the metal ion be bonded to the ligand solely by coordinate covalent bonds forming the ring structure. In either case, both are definitions that describe a metal ion and a ligand forming a heterocyclic ring.

A chelate is a definite structure resulting from precise requirement of synthesis. Proper conditions must be present for chelation to take place, particularly under the more modern definition. These conditions include proper mole ratios of ligands to metal ions, pH and solubility of reactants. Generally, for chelation to occur, all components are dissolved in solution and are either ionized or of appropriate electronic configuration in order for coordinate covalent bonding and/or ionic bonding between the ligand and the metal ion to occur.

Chelation can be confirmed and differentiated from mixtures of components by infrared spectra through comparison of the stretching of bonds or shifting of absorption caused by bond formation. As applied in the field of mineral nutrition, there are two allegedly "chelated" products which are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed protein. Such products are referred to as the specific metal proteinate, e.g., copper proteinate, zinc proteinate, etc.

The American Association of Feed Control Officials (AAFCO) has also issued a definition for an amino acid chelate. It is officially defined as the product resulting from the reaction of a metal ion from a soluble metal salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, e.g., iron amino acid chelate, copper amino acid chelate, zinc amino acid chelate, etc.

An "amino acid chelate," when properly formed, is a stable product having one or more five-membered rings formed by reaction between the carboxyl oxygen, and the $\alpha$-amino group of an $\alpha$-amino acid with the metal ion. Such a five-membered ring is defined by the metal atom, the carboxyl oxygen, the carbonyl carbon, the a-carbon and the $\alpha$-amino nitrogen. The actual structure will depend upon the ligand to metal mole ratio and whether the carboxyl oxygen forms a coordinate covalent bond or an ionic bond with the metal ion. Generally, the ligand to metal mole ratio is at least 1:1 and is preferably 2:1 but, in certain instances, may be 3:1 or even 4:1. Most typically, an amino acid chelate may be represented at a ligand to metal ratio of 2:1 according to Formula 1 as follows:

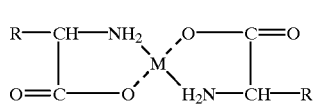

Formula 1

In the above formula, the dashed lines represent coordinate covalent bonds, covalent bonds or ionic bonds and the solid lines represent covalent bonds or coordinate covalent bonds (i.e., bond between the metal and the $\alpha$-amino groups). When R is H, the amino acid is glycine which is the simplest of the $\alpha$-amino acids. However, R could be representative of any other of the other twenty or so naturally occurring amino acids derived from proteins. Regarding the sulfur-containing amino acids, when R is —$CH_2$—$CH_2$—S—$CH_3$, the amino acid is methionine, and when R is $CH_2$—SH, the amino acid is cysteine. Further, two cysteine molecules bonded together by a disulfide bond form the amino acid cystine. Despite the different side chains, all of the amino acids have the same configuration for the positioning of the carboxyl oxygen and the $\alpha$-amino nitrogen with respect to the metal ion. In other words, the chelate ring is defined by the same atoms in each instance.

The reason a metal atom can accept bonds over and above the oxidation state of the metal is due to the nature of chelation. For example, at the $\alpha$-amino group of an amino acid, the nitrogen contributes to both of the electrons used in the bonding. These electrons fill available spaces in the d-orbitals forming a coordinate covalent bond. Thus, a metal ion with a normal valency of +2 can be bonded by four bonds when fully chelated. In this state, the chelate is completely satisfied by the bonding electrons and the charge on the metal atom (as well as on the overall molecule) is zero. As stated previously, it is possible that the metal ion be bonded to the carboxyl oxygen by either coordinate covalent bonds or ionic bonds. However, the metal ion is typically bonded to the $\alpha$-amino group by coordinate covalent bonds only.

The structure, chemistry and bioavailability of amino acid chelates is well documented in the literature, e.g. Ashmead et al., *Chelated Mineral Nutrition,* (1982), Chas. C. Thomas Publishers, Springfield, Ill.; Ashmead et al., *Intestinal Absorption of Metal Ions,* (1985), Chas. C. Thomas Publishers, Springfield, Ill.; Ashmead et al., *Foliar Feeding of Plants with Amino Acid Chelates,* (1986), Noyes Publications, Park Ridge, N.J.; U.S. Pat. Nos. 4,020,158; 4,167,564; 4,216,143; 4,216,144; 4,599,152; 4,774,089; 4,830,716; 4,863,898 and others. Further, flavored effervescent mixtures of vitamins and amino acid chelates for administration to humans in the form of a beverage are disclosed in U.S. Pat. No. 4,725,427.

One advantage of amino acid chelates in the field of mineral nutrition is attributed to the fact that these chelates are readily absorbed in the mucosal cells by active transport or in plant cells as though they were solely amino acids. In other words, in the case of animal nutrition, the minerals are absorbed along with the amino acids as a single unit utilizing the amino acids as carrier molecules. Therefore, the problems associated with the competition of ions for active sites and the suppression of specific nutritive mineral elements by others are avoided.

Zinc (Zn) is an essential trace mineral that is present in nearly all animal cells, including humans. However, zinc is highly concentrated in specialized areas of the brain, pancreas and adrenal gland. Further, zinc has structural, enzymatic and regulatory roles in the body of animals. In fact, well over 70 enzymes require zinc for activity, including RNA polymerases. Further, zinc is essential for proper growth, tissue repair, sexual maturity (i.e., reproductive organs, prostate functions and male hormone activity), reproductive performance, blood stability, protein synthesis, digestion and metabolism of phosphorus, and immunity.

Deficiencies in zinc may result in delayed sexual maturity, prolonged healing of wounds, white spots on the finger nails, retarded growth, stretch marks, fatigue, decreased alertness, and susceptibility to infections. However, though deficiencies may take a part in causing the above heath-related issues, excessive zinc has been linked to impaired immune function, altered blood cholesterol levels, and a wide range of blood abnormalities. This being the case, it would be important for one to get his or her daily requirement of zinc by a source that is predictable regarding bioavailability and at a weight percentage that is advantageous.

The U.S. Recommended Daily Allowance (RDA) for zinc is as follows: for babies from birth to 1 year, 5 mg per day; for children 1 to 10 years, 10 mg per day; for men and boys 11 to 51 years, 15 mg per day; for women and girls 11 to 51 years, 12 mg per day; for pregnant women, 15 mg per day; for nursing mothers in the first 6 months, 19 mg per day; and for nursing mothers in the second 6 months, 16 mg per day.

Turning to the nourishment of non-human animals, the major sources of zinc approved by AAFCO for use in animal feed are zinc oxide and zinc sulfate. Zinc oxide is the most widely-used source of zinc in the animal feed industry because it has the highest zinc content and has been the most economical source of zinc on a per-unit basis. Zinc oxide suitable for animal use in feed is usually manufactured by the Waelz Kiln process. In the Waelz Kiln process, zinc-bearing ores are roasted, forming a zinc fume. The zinc fume is collected in a large collector and is densified. The very high temperatures used in this process drive off most of the residual heavy metals. Alternatively, zinc oxide for use in the feed industry may also be manufactured by the French process. The French process usually results in a higher zinc content (e.g. 78–80% zinc) than that produced by the Waelz Kiln process. However, the French process produces a powder that is more difficult to handle in animal feed mixes and is generally more expensive on a per-unit of zinc basis.

Zinc sulfate is also regularly used in animal feed products as an economic alternative to zinc oxide. Essentially, to make zinc sulfate, zinc is dissolved in sulfur-containing acid and spray dried. In either case, whether zinc oxide or zinc sulfate is used in an animal feed product, there are issues that work to prevent some of the zinc consumed by the animal from being bioavailable.

More recently, there has been a growing interest in compounds containing zinc and amino acids. For example, in U.S. Pat. No. 5,061,815, a zinc lysine complex is disclosed which also includes a halide, sulfate, phosphate, carbonate or acetate ion. This product is normally used in poultry and/or livestock rations. Particularly, the compound zinc lysine sulfate is commercially used and is alleged to provide rapid zinc absorption into the gastrointestinal tract of animals. The specific structure is comprised of one ion of zinc which is bound to one molecule of the amino acid lysine with an associated sulfate ion, i.e., 1:1 ligand to metal molar ratio.

Based upon what is known in the art presently, it would be useful to provide a zinc compound that is stable and is also more bioavailable than the inorganic zinc compounds previously known in the art. Further, it would be useful to provide a zinc compound that is formed by chelating zinc ions to a mixture glycine and a sulfur-containing amino acid, such that the weight percentage of zinc to the ligand may be more easily controlled and the zinc may be targeted to specific tissues or organs. These needs and others are fulfilled by the zinc amino acid chelate compositions of the present invention.

OBJECTS AND SUMMARY OF THE INVENTION

It is an object of the present invention to provide a zinc amino acid chelate formulation comprised of two amino acids (i.e., glycine and a sulfur-containing amino acid) such that a desired zinc content weight percentage may be achieved at from about a 1:1 to 2:1 amino acid ligand to metal molar ratio.

It is another object of the present invention to provide a stable and highly bioavailable zinc source for use in feed for livestock and poultry.

It is still another object of the present invention to provide a zinc source that is highly bioavailable such that the minimum daily requirement for zinc may more easily be met.

These and other objects may be accomplished by providing a zinc amino acid chelate formulation comprising zinc ions being chelated by an amino acid ligand mixture comprising glycine and a sulfur-containing amino acid wherein the ligand to zinc molar ratio is from about 1:1 to 2:1 and wherein the glycine to sulfur-containing amino acid molar ratio is between about 1:6 to 6:1.

DETAILED DESCRIPTION OF THE INVENTION

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the content clearly dictates otherwise.

The term "chelate" is intended to cover both the traditional definition and the more contemporary definition as cited previously. Specifically, for purposes of the present invention, chelate is meant to include metal ions bonded to ligands forming heterocyclic rings. The bonds may be coordinate covalent, covalent and/or ionic at the carboxyl oxygen group. However, at the α-amino group, the bond is typically a coordinate covalent bond.

"Amino acid ligand mixture" is meant to include amino acids that are first mixed and then added to a zinc source as well as amino acids that are mixed in situ. In other words, it does not matter whether the amino acids are mixed prior to reaction with the zinc ions, mixed while in the presence of the zinc ions, or mixed after one of the amino acids has reacted with the zinc ions.

With this in mind, the present invention is drawn to a zinc amino acid chelate formulation comprising zinc ions being chelated by an amino acid ligand mixture comprising glycine and a sulfur-containing amino acid wherein the ligand to zinc molar ratio is from about 1:1 to 2:1 and wherein the glycine to sulfur-containing amino acid molar ratio is between about 1:6 to 6:1. Though the molar ratio of glycine to the sulfur-containing amino acid may be from about 1:6 to 6:1, it is preferred that the molar ratio of glycine to the sulfur-containing amino acid is from about 2:3 to 6:1, and most preferably from about 5:4 to 5:2.

As a practical matter, when the ligand to zinc molar ratio is about 2:1, the zinc ion and the amino acid ligand mixture will likely form a composition containing zinc bisglycinate, a zinc amino acid chelate having two sulfur-containing amino acid ligands, and a zinc amino acid chelate having one glycine ligand and one sulfur-containing amino acid ligand. When the ligand to zinc molar ratio is about 1:1, at least a portion of the chelates are zinc glycinates and at least a portion of the chelates are zinc amino acid chelates having a sulfur-containing amino acid ligand.

One of the other objectives of the present invention is to provide a compound where the average theoretical zinc content is from about 18 to 30% by weight for embodiments having a 2:1 ligand to metal molar ratio. However, it is preferred that the average theoretical zinc content is from about 21 to 27% by weight. Alternatively, for embodiments having a 1:1 ligand to metal molar ratio, the present invention provides a compound having an average theoretical zinc content from about 30 to 47% by weight. However, it is preferred that the average theoretical zinc content is from about 34 to 44% by weight. These weight ratios may be realized by reacting appropriate amounts of glycine and the sulfur-containing amino acid in an aqueous environment to form the zinc amino acid chelates disclosed herein. However, it is important to note that the weight percentages of both the 2:1 and the 1:1 embodiments described above are theoretical ranges which are based solely upon the zinc weight percentage as compared to the zinc amino acid chelate alone. In many circumstances, the actual weight percentage of zinc in the compound may be reduced due to the presence of other anions which may or may not be complexed to the amino acid chelate.

Regarding embodiments where an amino acid chelate having a 1:1 ligand to metal molar ratio is formed in accordance with the present invention, a sulfate anion will likely complex with the amino acid chelate. The general formula for such an amino acid chelate is $[Zn(AA)SO_4]^-H^+$ where AA is either a sulfur-containing amino acid or glycine, though both types of amino acid chelates, i.e., $[Zn(Gly)SO_4]^-H^+$ and $[Zn(Met)SO_4]^-H^+$, will be present in the composition.

Regarding embodiments where an amino acid chelate having a 2:1 ligand to metal molar ratio is formed in accordance with the present invention, any sulfate anion present in the composition will likely not complex with the amino acid chelate. However, each amino acid chelate molecule within the total composition will be comprised of zinc and two amino acid ligands where the ligands are selected from 1) two glycines, 2) one glycine and one sulfur-containing amino acid, or 3) two sulfur-containing amino acids. Thus, each individual chelate molecule will have one of three molecular weights. Therefore, when referring to the total zinc content by weight, the average zinc content over the entire composition will generally be described, either as a theoretical percentage or as an actual weight percentage.

The zinc of the amino acid chelates are preferably provided by one of many zinc sources such as zinc sulfate, zinc oxide, zinc chloride, zinc acetate, and combinations thereof, though other sources may be used as known by those skilled in the art. However, zinc sulfate is the most preferred zinc source. Additionally, fillers and/or drying agents including mineral oil, soy flour, wheat flour, rice flour, silica, maltodextrin, microcrystalline cellulose, and is others may also be added to the chelates of the present invention.

In the area of animal nutrition, one advantage of using these chelates over zinc oxide or zinc sulfate is that the zinc amino acid chelates of the present invention are regarded as organic. In order to be absorbed, inorganic zinc compounds must first dissolve in the stomach or intestines and the zinc must complex with an organic compound in the gastrointestinal tract before it can be absorbed. If there are not enough of these organic complexing compounds present in the gastrointestinal tract in sufficient concentrations, adequate absorption of zinc may not occur, despite the presence of an abundance of zinc oxide, zinc sulfate, or other inorganic zinc compounds. Further, the presence of high concentrations of calcium, phosphates, other divalent cations, phytates, or fiber may also interfere with the absorption of zinc by forming insoluble complexes with zinc.

The use of multiple amino acids for the ligand component of the amino acid chelate also has advantages. First of all, because different amino acids have different molecular weights, the weight percentage of the metal may be modulated by utilizing more or less of each amino acid. For example, if a higher weight percentage of a metal is desired, then more glycine (the amino acid having the lowest molecular weight) and less of the heavier sulfur-containing amino acid such as methionine may be used. If one desires to lower the weight percentage of a metal, then less glycine may be used.

In the case of zinc, there are also advantages of using a sulfur-containing amino acid over the use of other amino acids as the amino acid ligand. Some of these advantages are taught in U.S. Pat. No. 4,863,898, the entire teachings of which are incorporated herein by reference. Specifically, methionine, a sulfur-containing amino acid, is known to promote the healing of wounds, ovaries, and the liver. Further, cysteine is thought to be beneficial in targeting the brain. Since zinc is known to be used for tissue repair and reproductive development, the use of one of these sulfur-containing amino acids as a portion of the ligand component in the context of the present composition of matter would be valuable.

EXAMPLES

The following examples illustrate how the zinc amino acid chelates of the present invention are prepared and used. The following examples should not be considered as limitations of the present invention, but should merely teach how to make the best known amino acid chelates based upon current experimental data.

Example 1

A mixture of 42.93 grams of zinc sulfate, 12 grams of methionine, and 30 grams of glycine were reacted in an aqueous environment for 60 minutes at a temperature of about 65 to 70° C. This reaction produced a zinc amino acid chelate having a ligand component to metal molar ratio of about 2:1, a theoretical average zinc content of about 26.8% by weight, and a glycine to methionine molar ratio of about 5:2. Due to the presence of the sulfate anion, the actual average zinc weight percentage was about 18.2%.

Example 2

A mixture of 42.93 grams of zinc sulfate, 19 grams of cysteine, and 23.61 grams of glycine were reacted in an aqueous environment for 60 minutes a temperature of about 65 to 70° C. This reaction produced 63.5 grams of a zinc amino acid chelate having a ligand component to metal molar ratio of about 2:1, a theoretical average zinc content of about 26.6% by weight, and a glycine to cysteine molar ratio of about 5:4. Due to the presence of the sulfate anion, the actual average zinc weight percentage was about 18.1%.

Example 3

A mixture of 42.93 grams of zinc sulfate, 6 grams of methionine, and 15 grams of glycine were reacted in an aqueous environment for 60 minutes at a temperature of about 65 to 70° C. This reaction produced a zinc amino acid chelate having a ligand component to metal molar ratio of about 1:1, a theoretical average zinc content of about 42.4% by weight, and a glycine to methionine molar ratio of about 5:2. Due to the presence of the sulfate anion, the actual average weight percentage of zinc was about 24.1%. Additionally, the product produced may be described by the general formula $[Zn(AA)SO_4]^-H^+$ where AA is either a methionine or glycine amino acid, though both varieties would be present in the overall composition.

Example 4

A mixture of 42.93 grams of zinc sulfate, 9.5 grams of cysteine, and 11.8 grams of glycine were reacted in an aqueous environment for 60 minutes a temperature of about 65 to 70° C. This reaction produced 63.5 grams of a zinc amino acid chelate having a ligand component to metal molar ratio of about 1:1, an actual average zinc content of about 24% by weight, and a glycine to cysteine molar ratio of about 5:4. Additionally, the product produced may be described by the general formula $[Zn(AA)SO_4]^-H^+$ where AA is either a cysteine or glycine amino acid, though both varieties would be present in the final composition. In this example, the theoretical zinc content has not been calculated. However, the theoretical weight percentage for zinc in the amino acid chelate alone would be significantly higher than the actual weight percentage as disclosed above.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A zinc amino acid chelate formulation comprising zinc ions being chelated by an amino acid ligand mixture comprising glycine and a sulfur-containing amino acid wherein the ligand to zinc molar ratio is from about 1:1 to 2:1 and wherein the glycine to sulfur-containing amino acid molar ratio is between about 1:6 to 6:1.

2. A zinc amino acid chelate formulation as in claim 1 wherein the ligand mixture to zinc molar ratio is about 2:1.

3. A zinc amino acid chelate formulation as in claim 2 wherein the zinc ion and the amino acid ligand mixture form a composition comprising zinc bisglycinate, a zinc amino acid chelate having two sulfur-containing amino acid ligands, and a zinc amino acid chelate having one glycine ligand and one sulfur-containing amino acid ligand.

4. A zinc amino acid chelate formulation as in claim 2 wherein the molar ratio of the glycine to the sulfur-containing amino acid is from about 2:3 to 6:1.

5. A zinc amino acid chelate formulation as in claim 2 wherein the molar ratio of the glycine to the sulfur-containing amino acid is from about 5:4 to 5:2.

6. A zinc amino acid chelate formulation as in claim 5 wherein the molar ratio of the glycine to the sulfur-containing amino acid is about 5:4.

7. A zinc amino acid chelate formulation as in claim 5 wherein the molar ratio of the glycine to the sulfur-containing amino acid is about 5:2.

8. A zinc amino acid chelate formulation as in claim 2 wherein the theoretical zinc content is from about 18 to 30% by weight.

9. A zinc amino acid chelate formulation as in claim 8 wherein the theoretical zinc content is from about 21 to 27% by weight.

10. A zinc amino acid chelate formulation as in claim 2 wherein the sulfur-containing amino acid is methionine.

11. A zinc amino acid chelate formulation as in claim 2 wherein the sulfur-containing amino acid is cysteine.

12. A zinc amino acid chelate formulation as in claim 2 wherein the sulfur-containing amino acid is cystine.

13. A zinc amino acid chelate formulation as in claim 2 prepared by reacting zinc, a sulfur-containing amino acid, and glycine in an aqueous environment.

14. A zinc amino acid chelate formulation as in claim 2 wherein the zinc is provided by zinc sulfate, zinc oxide, zinc chloride, zinc acetate, and combinations thereof.

15. A zinc amino acid chelate formulation as in claim 14 wherein the zinc is provided by zinc sulfate.

16. A zinc amino acid chelate formulation as in claim 10 wherein the sulfur-containing amino acid is a combination of D-methionine and L-methionine.

17. A zinc amino acid chelate formulation as in claim 10 wherein the sulfur-containing amino acid is L-methionine.

18. A zinc amino acid chelate formulation as in claim 10 wherein the sulfur-containing amino acid is D-methionine.

19. A zinc amino acid chelate formulation as in claim 2 further comprising fillers and drying agents selected from the group consisting of mineral oil, soy flour, wheat flour, rice flour, silica, maltodextrin, microcrystalline cellulose, and combinations thereof.

20. A zinc amino acid chelate formulation as in claim 1 wherein the ligand mixture to zinc molar ratio is about 1:1.

21. A zinc amino acid chelate formulation as in claim 20 wherein at least a portion of the chelates are zinc glycinates and at least a portion of the chelates are zinc chelates having a sulfur-containing amino acid ligand.

22. A zinc amino acid chelate formulation as in claim 20 wherein the molar ratio of the glycine to the sulfur-containing amino acid is from about 2:3 to 6:1.

23. A zinc amino acid chelate formulation as in claim 22 wherein the molar ratio of the glycine to the sulfur-containing amino acid is from about 5:4 to 5:2.

24. A zinc amino acid chelate formulation as in claim 23 wherein the molar ratio of the glycine to the sulfur-containing amino acid is about 5:4.

25. A zinc amino acid chelate formulation as in claim 23 wherein the molar ratio of the glycine to the sulfur-containing amino acid is about 5:2.

26. A zinc amino acid chelate formulation as in claim 20 wherein the theoretical zinc content is from about 30 to 47% by weight.

27. A zinc amino acid chelate formulation as in claim 26 wherein the theoretical zinc content is from about 34 to 44% by weight.

28. A zinc amino acid chelate formulation as in claim 20 wherein the sulfur-containing amino acid is methionine.

29. A zinc amino acid chelate formulation as in claim 20 wherein the sulfur-containing amino acid is cysteine.

30. A zinc amino acid chelate formulation as in claim 20 wherein the sulfur-containing amino acid is cystine.

31. A zinc amino acid chelate formulation as in claim 20 prepared by reacting zinc, a sulfur-containing amino acid, and glycine in an aqueous environment.

32. A zinc amino acid chelate formulation as in claim 20 wherein the zinc is provided by zinc sulfate, zinc oxide, zinc chloride, zinc acetate, and combinations thereof.

33. A zinc amino acid chelate formulation as in claim 32 wherein the zinc is provided by zinc sulfate.

34. A zinc amino acid chelate formulation as in claim 28 wherein the sulfur-containing amino acid is a combination of D-methionine and L-methionine.

35. A zinc amino acid chelate formulation as in claim 28 wherein the sulfur-containing amino acid is L-methionine.

36. A zinc amino acid chelate formulation as in claim 28 wherein the sulfur-containing amino acid is D-methionine.

37. A zinc amino acid chelate formulation as in claim 20 further comprising fillers and drying agents selected from the group consisting of mineral oil, soy flour, wheat flour, rice flour, silica, maltodextrin, microcrystalline cellulose, and combinations thereof.

* * * * *